United States Patent
Harran et al.

(10) Patent No.: US 7,622,289 B2
(45) Date of Patent: Nov. 24, 2009

(54) ORNITHINE AMINOTRANSFERASE (OAT): A TARGET FOR ANTICANCER DRUGS

(75) Inventors: Patrick Harran, Dallas, TX (US); Xiaodong Wang, Dallas, TX (US); Gelin Wang, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 393 days.

(21) Appl. No.: 11/451,926

(22) Filed: Jun. 12, 2006

(65) Prior Publication Data

US 2007/0287679 A1 Dec. 13, 2007

(51) Int. Cl.
C12N 9/10 (2006.01)
C12N 15/00 (2006.01)
C12Q 1/00 (2006.01)
C12Q 1/48 (2006.01)
G01N 33/53 (2006.01)
A61K 38/51 (2006.01)
A01N 25/00 (2006.01)
C12P 21/04 (2006.01)

(52) U.S. Cl. .......................... 435/193; 435/4; 435/7.1; 435/15; 435/69.1; 435/71.1; 435/440; 514/789; 424/94.5

(58) Field of Classification Search .................. None
See application file for complete search history.

(56) References Cited

OTHER PUBLICATIONS

Branden et al. Introduction to Protein Structure, Garland Publishing Inc., New York, p. 247, 1991.*
Williams et al. Therapeutic anticancer efficacy of a synthetic diazonamide analog in the absence of overt toxicity. Proc Natl Acad Sci U S A. Feb. 13, 2007;104(7):2074-9. Epub Feb. 7, 2007.*
Wang et al. Diazonamide toxins reveal an unexpected function for ornithine delta-amino transferase in mitotic cell division. Proc Natl Acad Sci U S A. Feb. 13, 2007;104(7):2068-73. Epub Feb. 7, 2007.*

* cited by examiner

Primary Examiner—Yong D Pak
(74) Attorney, Agent, or Firm—Richard Aron Osman

(57) ABSTRACT

Ornithine δ-aminotransferase (OAT) facilitates microtubule assembly in addition to its aminotransferase activity in mitochondria. An N-terminal proteolysis of the first 17 amino acids of OAT block its transport to the mitochondria. The resultant truncated protein (OATC) forms specific complexes with mitotic spindle promoting proteins such as Eg5 and takes on a Ran-dependent spindle-assembly activity. Methods and compositions for inhibiting mitotic spindle assembly in a cell by specifically inhibiting OAT, and methods for screening for inhibitors of (1) the spindle-assembly function of OAT, (2) the protease that N-truncates OAT, (3) the OAT/RanGTP association and (4) the OAT/Eg5 association are disclosed.

6 Claims, No Drawings

ORNITHINE AMINOTRANSFERASE (OAT): A TARGET FOR ANTICANCER DRUGS

This work was supported by National Cancer Institute Grant No. PO1 CA95471. The U.S. government may have rights in any patent issuing on this application.

BACKGROUND OF THE INVENTION

The field of the invention is ornithine δ-aminotransferase (OAT) as a target for anticancer drugs.

The segregation of replicated chromosomes during cell division is executed by the mitotic spindle, a molecular machine assembled transiently for this purpose. The spindle is comprised of filamentous polymerized heterodimeric tubulin radiating from two opposing spindle poles. Tightly regulated microtubule dynamics are necessary for robust bipolar spindle assembly and to ensure fidelity in the separation of sister chromatids at anaphase [1-4]. The small GTPase Ran plays a regulatory role in the initiation of mitotic spindle assembly [5]. At the onset of mitosis, RanGTP is concentrated around condensed chromosomes. Analogous to its role in nucleocytoplasmic transport during interphase, RanGTP stimulates the release of sequestered spindle assembly factors (SAFs) such as NuMA, TPX2, and/or XCTK2 from transport receptors importin β/α and renders them active. These factors, in turn, locally promote microtubule polymerization at spindle poles [6-8].

Diazonamide A (compound 1, Table 1) is a small molecule toxin originally isolated from tissue homogenates of the marine ascidian *Diazona angulata* [9].

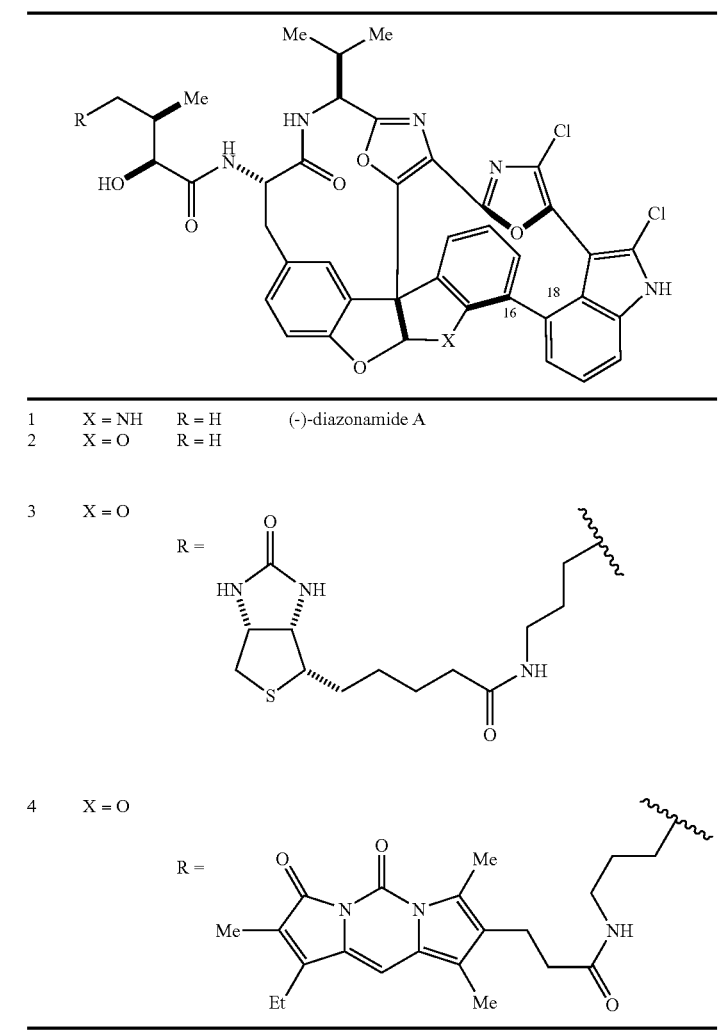

Purified 1 inhibits cultured human cancer cell growth at low nanomolar concentrations. Early analyses at the NCI demonstrated diazonamide toxicity is manifest as an M-phase growth arrest wherein treated cells fail to assemble bipolar mitotic spindles and accumulate in the tetraploid state. COMPARE pattern analysis of observed cytotoxic/cytostatic activities implied a mechanistic correlation between diazonamide and microtubule de-polymerizing agents such as maytansine and vinblastine. Along these lines, 1 was found to inhibit purified tubulin polymerization in vitro as well as dissipate the tubulin cytoskeleton in cells at high concentrations. However, diazonamide A did not compete with vinca alkaloids or nocadazole for tubulin binding [10]. Our own experiments with 1 in BS-C-1 and PTK2 culture showed that, at GI$_{50}$ concentrations, the molecule had little impact on interphase microtubules—suggesting its catastrophic effect on spindle microtubules was indirect. To test this possibility, a synthetic variant of diazonamide A (2, Table 1) was prepared [11]. Like the natural product, 2 shows potent antimitotic activity in cell culture and induces spindle abnormalities during mitosis indistinguishable from those caused by 1. A peripherally biotinylated form of 2 (namely 3, Table 1) also retains this activity (vide infra).

The observation that neither 3 nor a radio-labeled congener of 2 binds specifically to tubulin or microtubules in vitro was the starting point for our studies to determine the functional target of diazonamide A.

SUMMARY OF THE INVENTION

One aspect of the invention is a method to identify an inhibitor of ornithine δ-aminotransferase (OAT)-facilitated spindle formation comprising the steps of: (a) contacting a spindle assembly system with an OAT-binding agent under conditions wherein, but for the presence of the agent, the system provides a first spindle assembly; and (b) detecting a second, agent-biased spindle assembly, wherein a defective agent-biased spindle assembly compared to the first spindle assembly indicates that the agent is an inhibitor of OAT-facilitated spindle formation.

In one embodiment the determining step comprises performing a competitive binding assay with the OAT, the candidate agent, and a labeled OAT-binding compound. In various embodiments the spindle assembly system comprises Hela cells or *Xenopus* egg extracts. The method may comprise the further step of determining whether the agent inhibits OAT ornithine aminotransferase activity.

Another method of the invention identifies an inhibitor of OAT proteolysis. The method comprises incubating a mixture comprising OAT, a candidate agent, and an OAT-protease under conditions wherein, but for the presence of the agent, the protease cleaves the OAT to form N-truncated OAT beginning with Val18 at a first amount of proteolysis; and detecting a second, agent-biased amount of proteolysis of the OAT, wherein a lesser agent-biased amount of proteolysis compared to the first amount indicates that the agent is an inhibitor of OAT proteolysis. The mixture may comprise an OAT-protease containing cytoplasmic extract. In one embodiment, the detecting is by Western blot analysis.

Another method identifies an inhibitor of an OAT and OAT-associated protein (OAP) association. The method comprises incubating a mixture comprising OAT, a candidate agent, and an OAP under conditions wherein, but for the presence of the agent, the OAT and OAP engage in a first amount of association, wherein the OAP is selected from Ran and Eg5; and detecting a second, agent-biased amount of OAT-Ran association, wherein a lesser agent-biased amount of OAT-OAP association compared to the first amount indicates that the agent is an inhibitor of OAT-OAP association. In a specific embodiment the OAP is Eg5 and the association is binding. The method may comprise the further step of determining whether the agent inhibits OAT ornithine aminotransferase activity.

Another aspect of the invention is an isolated N-truncated OAT consisting essentially of amino acids 18-439 of human OAT (GenBank Accession No. AAH00965.1).

Another method of the invention is inhibiting mitotic spindle assembly in a cell by a method comprising: contacting the cell with an OAT-specific inhibitor selected from the group consisting of an siRNA, antisense oligonucleotide, and an antibody; and detecting an inhibition of mitotic spindle assembly in the cell.

DETAILED DESCRIPTION OF SPECIFIC EMBODIMENTS OF THE INVENTION

We show that ornithine δ-aminotransferase (OAT) promotes microtubule assembly in addition to its aminotransferase activity in mitochondria. An N-terminal proteolysis of the first 17 amino acids of OAT blocks its transport to the mitochondria. The resultant truncated protein (OATC) forms specific complexes with mitotic spindle promoting proteins such as Eg5 and takes on a Ran-dependent spindle-assembly activity. The invention provides methods and compositions for inhibiting mitotic spindle assembly in a cell by specifically inhibiting OAT, and methods for screening for inhibitors of (1) the spindle-assembly function of OAT, (2) the protease that N-truncates OAT, (3) the OAT/RanGTP association and (4) the OAT/Eg5 association.

In one assay for screening inhibitors of OAT-facilitated spindle formation, candidate agents are first tested for their ability to bind OAT. The OAT-binding agents are then tested in a spindle assembly system to determine if they reduce OAT-facilitated spindle formation activity. Any suitable binding assay can be used to determine if a candidate agent binds OAT. As one example, a competitive binding assay is performed by incubating a mixture comprising OAT, a labeled (control) agent known to specifically bind OAT (e.g. diazonamide A), and a candidate binding agent, under conditions wherein, but for the presence of the candidate binding agent, the labeled agent specifically binds the OAT. Typically the OAT is recombinant and/or purified and is bound to a solid phase to facilitate removal of unbound agents in the binding assay. Candidate agents that compete with labeled agent for OAT-binding, as indicated by a reduction in OAT-bound label, are identified as putative OAT-binding agents. Specific binding between OAT and the candidate agent can be confirmed by a variety of methods, such as affinity purification of OAT by the putative binding agent (e.g. see Example 2), fluorescence perturbation, fluorescence correlation spectroscopy, etc.

A spindle assembly assay is performed by contacting a candidate agent with a spindle assembly system under conditions wherein, but for the presence of the agent, the system assembles a first spindle; and detecting a second, agent-biased spindle assembly, wherein an agent-biased spindle assembly compared to the first spindle assembly indicates that the agent is an inhibitor of OAT-facilitated spindle formation. Suitable spindle assembly systems include *Xenopus* egg extracts [5], Hela cells [22], COS-7 cells [23, 24], CHO cells [24], U20S cells [25], etc. An agent-biased spindle assembly is a spindle-assembly that has a phenotype that differs from that of the first spindle assembly (i.e. the normal control). For example, inhibition of OAT by diazonamide A blocks normal bipolar spindle assembly in Hela cells and causes a multi-pole spindle phenotype with misaligned chromosomes (see Example 1). The spindle phenotypes are typically visualized by fixing the cells or cell extracts and differentially staining the α-tubulin and DNA [5]. Spindle assembly can also be visualized by live cell imaging [23, 24].

We have found that N-truncation of the first 17 amino acids of human OAT is required for it to take on its spindle-assembly function; the truncated protein begins with Val18. Accordingly, the invention provides an isolated N-truncated OAT protein that begins with Val18. This truncated protein is referred to herein as OATC. Purified or recombinant OATC can be used in the screening assays of the invention. In specific embodiments, the OATC is from a mammalian species and has an amino acid sequence that consists of a sequence that corresponds to amino acids 18-439 of human OAT (GenBank Nos. AAH00964.1; GI:12654287). OATs from numerous mammalian species have been identified that share high sequence identity with human OAT. Some examples include mouse (BAE26718.1; GI:74219159), rat (NP_071966.1; GI:11968102), and cow (AA102428.1; GI:73586966) OAT.

Another screening assay of the invention identifies inhibitors of the specific proteolysis that results in OATC. The assay comprises incubating a mixture comprising OAT, a candidate agent, and an OAT-protease under conditions wherein, but for the presence of the agent, the protease cleaves the OAT to form N-truncated OAT beginning with Val18 at a first amount of proteolysis; and detecting a second, agent-biased amount of proteolysis of the OAT, wherein a lesser agent-biased amount of proteolysis compared to the first amount indicates that the agent is an inhibitor of OAT proteolysis. The OAT-protease may be identified using methods to identify proteins that interact with OAT such as two-hybrid analysis or affinity purification. Interacting proteins are then tested in cleavage assays to identify the specific protease that cleaves OAT after residue 17. The protease can then be used in the screening assays in purified or recombinant form. Alternatively, the screening assay may use an OAT-protease containing cytoplasmic extract, such as a *Xenopus* egg extract. Various suitable protein cleavage assays can be used to detect candidate agents that inhibit the proteolysis of OAT to OATC. In a specific embodiment, a recombinant full-length OAT having a C-terminal His-tag is incubated with the OAT-protease in the presence or absence of a candidate agent and Western blot analysis with an anti-His antibody is performed to detect whether the candidate agent inhibits the proteolysis compared to the amount of proteolysis that occurs in the absence of the candidate agent (e.g. see Example 3).

Other assays of the invention identify inhibitors of OAT-OAT-associated protein (OAP) binding. Proteins that directly or indirectly bind OAT can be identified using routine methods such as two hybrid analysis or affinity purification such as coimmunoprecipitation. The assays comprise incubating a mixture comprising OAT, a candidate agent, and an OAP under conditions wherein, but for the presence of the agent, the OAT and OAP engage in a first, reference amount of binding; and detecting a second, agent-biased amount of OAT-OAP binding, wherein a lesser agent-biased amount of OAT-OAP binding compared to the first amount indicates that the agent is an inhibitor of OAT-OAP binding. In various embodiments the OAT-associated protein is Eg5 or Ran and the ability of a candidate agent to inhibit OAT/Eg5 or OAT/Ran binding is detected.

Any of the above-described screening assays my further comprise the additional step of determining whether the candidate agent inhibits OAT's ornithine aminotransferase activity (e.g. see Example 2). In some embodiments, inhibitors of OAT mitotic spindle assembly activity that do not inhibit OAT's aminotransferase activity are selected for development.

Another aspect of the invention is a method of inhibiting mitotic spindle assembly in a cell comprising contacting the cell with an OAT-specific inhibitor selected from the group consisting of an antisense oligonucleotide, an siRNA that inhibits OAT transcription or translation, and an antibody (e.g. intrabody); and detecting an inhibition of mitotic spindle assembly in the cell. The OAT-specific inhibitors are made using routine methods and are tested for ability to inhibit mitotic spindle assembly using the above-described screening assays. In a particular embodiment the OAT-specific inhibitor is siRNA (e.g. see Example 6, and ref. 23). The cell may be in vitro or in situ in a patient predetermined to be in need of a cell division blocking treatment. Preferred inhibitors inhibit the spindle assembly facilitating function of OAT without inhibiting its transferase activity.

EXAMPLE 1

Impact of Diazonamide A on Spindle Assembly Reactions in *Xenopus* Egg Extracts

Biotin conjugate 3 (Table 1) was prepared to facilitate isolation of diazonamide binding proteins using avidin-based affinity chromatography. Compound 3 inhibits HeLa cell growth similarly to 1 ($GI_{50}$=15 nM versus 5 nM). Eighteen hours following dosage with 30 nM 3, roughly 70% of cells were arrested in mitosis and showed a multi-pole spindle phenotype with misaligned chromosomes—a situation indistinguishable from that caused by 30 nM 1. As a negative control, seco analog 5 was synthesized:

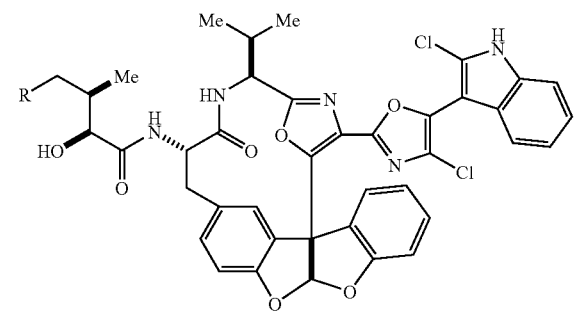

5

This molecule is identical to 3 except it lacks the biaryl linkage connecting carbons 16 and 18 (Table 1). This modification allows the bis(oxazoyl)indole motif to sample extended conformations and results in a thousand-fold loss of cellular activity.

Mitotic spindle assembly in *Xenopus* egg extracts was used to characterize this pair of diazonamide reagents. Similar to the situation in HeLa cells, 2-treated egg extracts did not support proper spindle assembly when provided sperm centromeres. Moreover, when compound 3 was conjugated to avidin-coated beads and the resultant material used to deplete egg extracts of putative diazonamide binding proteins, subsequent addition of sperm centromeres left condensed chromatin disorganized. Neither spindles nor microtubule asters formed around sperm DNA. Supplementing these depleted extracts with purified tubulin did not restore spindle formation. Notably, control compound 5-depleted extracts supported normal spindle assembly. Taken together, these data indicated compound 3 specifically removed a factor, other than tubulin, essential for spindle assembly.

EXAMPLE 2

Isolation of OAT as a Diazonamide Binding Protein

HeLa S100 was incubated with affinity matrices prepared from both compounds 3 (active) and 5 (control). Visualization of affinity-purified proteins by silver-stained SDS-PAGE revealed that two bands roughly 50 kDa in size were recovered specifically by the active compound matrix. Mass spectrometry identified both as ornithine δ-aminotransferase (OAT). To confirm this result, we further fractionated HeLa nuclear extract by Hitrap Q anion-exchange chromatography. Each eluted fraction was affinity probed for diazonamide binding proteins. For those fractions containing specific binding partners, the analysis was cleaner but results were the same. Polyclonal antibodies against full length human OAT (hOAT) and *Xenopus* OAT (xOAT) were subsequently raised and purified. Western blotting analysis of compound 3-based affinity purifications confirmed that the compound 3/OAT interaction was specific in both HeLa cells and *Xenopus* egg extracts. Pre-treatment of extracts with an excess of non-biotinylated substance 2 competitively blocked affinity purifications of OAT by 3.

To verify that diazonamide binds to OAT in cells, we synthesized a green-fluorescent version of the toxin (4, Table 1). Neither endogenous OAT nor other cellular components were visibly stained in HeLa cell culture by compound 4. However, when cells were induced to over-express Myc-tagged OAT harboring an N-terminal nuclear localization sequence (NLS), immunofluorescence with an anti-Myc antibody readily detected this form of OAT in nuclei. Moreover, such OAT over-expressing cells, and only those cells, were similarly stained by fluorescent compound 4. A merged image indicated that OAT and diazonamide derivative 4 co-localize in this experiment.

To determine if diazonamide binds to OAT directly, recombinant His-tagged hOAT was produced in bacteria, purified, and incubated with compound 3-coated avidin agarose. In this purified system, 3 retained the ability to affinity purify hOAT, indicating a direct interaction between the two. We next examined the impact of diazonamide binding on OAT enzymatic activity. Crude mitochondrial extracts from mouse liver were assayed for ornithine aminotransferase activity in the presence of increasing concentrations of compounds 2 or 3. Neither inhibited the conversion of L-ornithine to L-$\Delta^1$-pyrroline-5-carboxylic acid in this system. In contrast, 4-aminohex-5-ynoic acid, a characterized OAT inhibitor (12), suppressed the activity in a dose dependent manner.

EXAMPLE 3

OAT is N-Terminally Cleaved in *Xenopus* Egg Extracts in a Manner Distinct from its Mitochondrial Processing To directly test the function of OAT in mitosis, we incubated 2 FM recombinant full-length human OAT (hOAT) with a C-terminal His-tag to 300 μg of *Xenopus* egg extracts for 30 minutes at room temperature prior to Western blot analysis with an anti-His antibody. Results indicated that the polypeptide was truncated within 30 minutes at room temperature. This processing activity of egg extracts was saturated above 2 □M added hOAT. Truncated hOAT was re-purified using a nickel affinity column and its N-terminus was sequenced by Edman degradation. This experiment revealed cleavage had occurred after residue 17 (Gly), exposing a new N-terminus beginning with Val18. Cleavage specificity was confirmed by site-directed mutagenesis. Replacing Val18 with Asp affords a mutant no longer cleaved when incubated with *Xenopus* egg extracts. The processed form of OAT also specifically interacts with compound 3. Previous studies established that hOAT contains a 25-residue N-terminal mitochondrial targeting sequence that is cleaved upon mitochondrial entry (13). The alternate cleavage site identified in these studies indicates that OAT does not localize exclusively in mitochondria.

To assess the function of truncated OAT (OATC), HeLa cells were induced to express the truncated protein as a GFP fusion (hOATC-GFP). Because deletion of the first 17 amino acids eliminates a majority of the mitochondrial targeting sequence, hOATC-GFP accumulates primarily in the cytoplasm. Immunostaining with an antibody for α-tubulin revealed prominent microtubule aggregates in regions where hOATC-GFP had concentrated. The co-localization of hOATC-GFP and microtubule asters is similar to the situation found for a mutant of the nuclear mitotic apparatus protein (NuMA) lacking its NLS domain (NuMAΔNLS) (14). NuMA is a microtubule associated protein (MAP) with an established role in focusing spindle poles by promoting microtubule bundling. During interphase, NuMA is localized in the nucleus (15, 16). Mis-expression of NuMAΔNLS in the cytoplasm nucleates microtubules ectopically, as does hOATC-GFP.

EXAMPLE 4

OATC Promotes Microtubule Aster Formation in a Ran-dependent Manner

The parallel actions of hOATC-GFP and NuMAΔNLS implied OATC acts as a microtubule assembly factor. To probe this issue in the context of spindle assembly, His-tagged recombinant hOATC and xOATC (*Xenopus* OAT with a similar N-terminal truncation), were added to spindle assembly reactions in *Xenopus* egg extracts. Both generated tubulin asters separate from sperm chromatin—an observation consistent with OATC positively regulating microtubule assembly. However, OATC itself does not promote aster formation in the absence of sperm DNA. We reasoned that trace amounts of RanGTP diffusing outward from sperm DNA might enhance the action of OATC. To test this hypothesis, we turned to a system where Ran levels could be carefully specified. At a final concentration of 25 □M, a constitutively active mutant form of Ran, RanL43E, stimulates microtubule aster formation in egg extracts. At lower concentrations (6 □M), it fails to show this activity. However, in the presence of 20 □M xOATC, 6 □M RanL43E was sufficient to generate astral microtubules while adding BSA had no such potentiating effect. This data indicated OAT synergizes with Ran to promote microtubule assembly. Along these lines, 20 □M added xOATC partially rescued Ran-mediated aster formation in compound 3-depleted egg extracts. Observed asters in this case were formed stably in large numbers. However, they were smaller than those seen in non-depleted extracts. While this indicates that diazonamide depletion removed more than just OATC, it is clear that OAT was both a binding partner and functional target of diazonamide A. Human OATC showed activity similar to xOATC. Unlike OATC, full-length OAT does not stimulate microtubule assembly since the non-cleavable form of OAT (V18D) has no activity in Ran-stimulated aster formation.

EXAMPLE 5

OAT Interacts with Known Components of the Mitotic Spindle

Because the aster forming activity of OAT is dependent upon Ran, we sought to determine whether Ran regulates the interaction between diazonamide and OAT. *Xenopus* egg extracts were pre-incubated with Ran prior to addition of avidin-agarose beads coated with compound 3. In that case, aster formations proceeded normally after compound depletion. In fact, Western blot analysis of depleted protein revealed a marked decrease of OAT binding to diazonamide following Ran pre-treatment. The Ran signal masked or eliminated the diazonamide binding site on OAT.

Adding purified OATC to diazonamide-depleted extracts only partially restored aster-forming activity, suggesting other factors were removed along with OAT. To search for such components, we incubated compound 3-coated avidin agarose with *Xenopus* egg extracts and then probed the proteins associated with the matrix with antibodies against proteins known to function in mitosis. We found that, in a similar Ran-dependent fashion, the kinesin motor protein Eg5, a protein shown capable of crosslinking microtubule arrays and establishing spindle bipolarity, was coprecipitated with 3.

EXAMPLE 6

OAT is Required for Bipolar Spindle Assembly in HeLa Cells

OAT is well characterized as a mitochondrial matrix enzyme. In this context it regulates flux through the urea cycle and couples, indirectly, proline biosynthesis to the availability of fumarate for consumption in the TCA cycle (19). For reasons not completely understood, mutations in the human enzyme are associated with a progressive degeneration of the retina and choroid termed gyrate atrophy (20). Of the extensive biochemical and genetic information on OAT, none has previously connected the polypeptide to cell division. To examine whether OAT plays a role in proper spindle assembly, HeLa cells were treated with siRNA targeting endogenous OAT (corresponding to nucleotides 212-230 of GenBank Accession No. BC016928.1 (GI:16877349)). Three days post siRNA transfection, OAT expression was nearly eliminated. Relative to controls, OAT knock-down results in an accumulation of cells arrested in the G2/M phase of cell cycle. Roughly 50% of those mitotic cells assembled a characteristic multi-pole spindle structure having misaligned chromosomes—notably, an effect reminiscent of that seen upon diazonamide A treatment in this cell line. However, 50-60% of such cells die and this outcome was not blocked by the broad spectrum caspase inhibitor Z-VAD—indicating a form of necrosis, perhaps induced by mitotic catastrophe, was operating rather than apoptosis. Introducing a silent mutation at the siRNA target region of OAT within these cells reversed the effect, indicating the phenotype was due specifically to OAT loss. It was possible cell death resulted from a lack of endogenous OAT enzymatic activity. However, supplementing culture media with either L-arginine or L-ornithine failed to attenuate the rate of death or restore normal spindle assembly in OAT siRNA-treated cells. Taken together, these data indicate that siRNA-induced mitotic defects emanate from a function of OAT unrelated to its established role as a mitochondrial enzyme.

EXAMPLE 7

OAT-Deficient Embryonic Fibroblasts are Resistant to Low Concentrations of Diazonamide A Loss of OAT enzymatic activity correlates with the progressive onset of gyrate atrophy (GA). Proper development, however, seems not to require the protein (21). OAT knockout mice are viable and these animals allowed us to further examine OAT involvement in diazonamide cytotoxicity. Fibroblasts were isolated from OAT-/-mouse embryos along with those from wild-type littermates (MEFs). OAT protein was not detectable in MEFs from the OAT-/-animals. As shown by flow cytometry, MEFs from wild type animals responded predictably to dosage with compound 2; with an accumulation of cells arrested in G2/M phases of the cell cycle. In contrast, no such shift was observed in OAT-/-MEFs at low drug concentrations. Interestingly, an abnormally high percentage of OAT-/-cells exist in G2/M even prior to compound treatment, indicating there is a subtle defect in cell cycle progression in these populations.

The OAT locus has been examined in fibroblasts derived from GA patients wherein various point and nonsense mutations have been characterized (20). Such cell lines offered another means to solidify the connection between OAT, diazonamide, and its anti-mitotic properties. When wild-type human fibroblasts were exposed to 10 nM diazonamide A for 30 hrs, >60% of cells rounded up—indicative in this case of mitotic arrest. In contrast, fibroblast lines derived from gyrate atrophy patients harboring OAT point mutations at the initiator methionine, or R154L, R180T, or a W391 nonsense mutation were resistant to the compound. Among the mutant cell lines examined only R154L and R180T variants express OAT protein. Notably, neither mutant protein could be affinity purified with compound 3 despite being detected in crude cell extracts.

The foregoing examples and detailed description are offered by way of illustration and not by way of limitation. All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims

REFERENCES

1. A. Desai, T. J. Mitchison, *Annu Rev Cell Dev Biol* 13, 83 (1997).
2. E. Karsenti, I. Vernos, *Science* 294, 543 (Oct. 19, 2001).
3. S. L. Kline-Smith, C. E. Walczak, *Mol Cell* 15, 317 (Aug. 13, 2004).
4. C. E. Walczak, *Curr Opin Cell Biol* 12, 52 (February 2000).
5. A. Wilde, Y. Zheng, *Science* 284, 1359 (May 21, 1999).
6. R. E. Carazo-Salas et al., *Nature* 400, 178 (Jul. 8, 1999).
7. S. C. Ems-McClung et al., *Mol Biol Cell* 15, 46 (January 2004).
8. O. J. Gruss et al., *Cell* 104, 83 (Jan. 12, 2001).
9. J. Li, X. Chen, et al, *Angew Chem Int Ed Engl* 40, 2682 (Jul. 16, 2001).
10. Z. Cruz-Monserrate et al., *Mol Pharmacol* 63, 1273 (June 2003).
11. J. Li et al., *Angew Chem Int Ed Engl* 40, 4765 (Dec. 17, 2001).
12. M. J. Jung, N. Seiler, *J Biol Chem* 253, 7431 (Oct. 25, 1978).
13. M. Simmaco etal., *FEBS Lett* 199, 39 (Apr. 7, 1986).
14. C. Gueth-Hallonet et al., *Exp Cell Res* 225, 207 (May 25, 1996).
15. D. A. Compton et al, *J Cell Biol* 116, 1395 (March 1992).

16. A. Merdes et al., *Cell* 87, 447 (Nov. 1, 1996).
17. R. Giet et al., *J Biol Chem* 274, 15005 (May 21, 1999).
18. M. Y. Tsai et al., *Nat Cell Biol* 5, 242 (March 2003).
19. N. Seiler, *Curr Drug Targets* 1, 119 (September 2000).
20. L. C. Brody et al., *J Biol Chem* 267, 3302 (Feb. 15, 1992).
21. T. Wang et al., *Nat Genet* 11, 185 (October 1995).
22. S. Martin-Lluesma et al., *Science* 297, 2267 (September 2002).
23. J. Rosa et al., Mol Biol Cell: 17, 1483 (March 2006).
24. A. Young et al., Mol Biol Cell. 11, 2047 (June 2000).
25. H. A. Fisk et al., Proc Natl Acad Sci USA. 100, 14875 (December 2003).

The invention claimed is:

1. A method to identify an inhibitor of ornithine δ-aminotransferase (OAT)-facilitated spindle formation comprising the steps of:
   determining that a candidate agent binds an OAT that promotes spindle assembly; and
   contacting a spindle assembly system wherein spindle assembly is facilitated by the OAT, with the agent under conditions wherein the agent binds the OAT and thereby inhibits the spindle assembly resulting in a defective spindle assembly as compared with a control spindle assembly, and thereby identifies the agent as an inhibitor of OAT-facilitated spindle formation, wherein the OAT is wild-type N-truncated mammalian OAT beginning with Val18.

2. The method of claim 1 wherein the determining step comprises performing a competitive binding assay with the OAT, the candidate agent, and a labeled control OAT-binding diazonamide A compound.

3. The method of claim 1 wherein the spindle assembly system comprises Hela cells.

4. The method of claim 1 wherein the spindle assembly system comprises *Xenopus* egg extracts.

5. The method of claim 1 comprising the further step of determining whether the agent inhibits OAT ornithine aminotransferase activity.

6. The method of claim 1 wherein OAT is N-truncated human OAT beginning with Val18.

* * * * *

UNITED STATES PATENT AND TRADEMARK OFFICE
CERTIFICATE OF CORRECTION

| | | |
|---|---|---|
| PATENT NO. | : 7,622,289 B2 | Page 1 of 1 |
| APPLICATION NO. | : 11/451926 | |
| DATED | : June 12, 2006 | |
| INVENTOR(S) | : Harran et al. | |

It is certified that error appears in the above-identified patent and that said Letters Patent is hereby corrected as shown below:

The reservation of government rights clause at Col.1, lines 4-6 should read:

This work was supported by National Cancer Institute Grant No. PO1 CA95471. The U.S. government has rights in any patent issuing on this application.

Signed and Sealed this

Twenty-sixth Day of January, 2010

David J. Kappos
*Director of the United States Patent and Trademark Office*